United States Patent [19]

Umezawa et al.

[11] 3,932,374
[45] Jan. 13, 1976

[54] BLEOMYCINIC ACID AND PROCESS FOR PREPARING THEREOF

[75] Inventors: Hamao Umezawa, Tokyo; Yasushi Takahashi, Hoya; Tadashi Shirai, Musashino; Akio Fujii, Tokyo, all of Japan

[73] Assignee: Zaidan Hojin Biseibutsu Kagaku Kenkyu Kai, Tokyo, Japan

[22] Filed: June 13, 1974

[21] Appl. No.: 479,087

Related U.S. Application Data

[60] Division of Ser. No. 290,986, Sept. 21, 1972, Pat. No. 3,867,257, which is a continuation-in-part of Ser. No. 252,252, May 11, 1972, Pat. No. 3,843,448.

[30] Foreign Application Priority Data

May 15, 1971 Japan................................ 46-32232

[52] U.S. Cl............................ 260/112.5 R; 424/177
[51] Int. Cl.²................. C07C 103/52; A61K 37/00
[58] Field of Search................................ 260/112.5

[56] References Cited
UNITED STATES PATENTS 3,846,400    5/1974    Umerzawa et al............... 260/112.5

OTHER PUBLICATIONS

Umezawa et al.: J. of Antibiotics, 19A, 200–209 (1966).
Umezawa et al.: J. of Antibiotics, 19A, 210–215 (1966).
Takita et al.: J. of Antibiotics, 21, 79–80 (1968).
Takita et al.: J. of Antibiotics, 22, 237–239 (1969).

*Primary Examiner*—Lewis Gotts
*Assistant Examiner*—Reginald J. Suyat
*Attorney, Agent, or Firm*—Oblon, Fisher, Spivak, McClelland & Maier

[57] ABSTRACT

A process for preparing bleomycinic acid having a melting point of 228°–230°C. (decomposition) and an analysis of C : 40.80%, H : 5.29%, N : 16.45%, O : 24.78%, S : 4.53%, Cl : 3.37%, and Cu : 4.78% which is characterized by being soluble in water, difficultly soluble in methanol, acetic acid and dimethylsulfoxide, and insoluble in ethanol, ethyl acetate, acetone and ether, and which tests positive to Pauly and Ehrlich reactions but tests negative to ninhydrin, Sakaguchi, Dragendorf, Tollens, ferric chloride, Fehling and Molish reactions, and which has a maximum ultraviolet absorption spectrum at 246 m$\mu$ and 292 m$\mu$ and which has an infrared absorption spectrum bands at 3350, 1720, 1670, 1640, 1580, 1460, 1365, 1050, 770 (cm$^{-1}$), and which can be hydrolyzed to yield 2'-(2-aminoethyl)-2,4'-bithiazole-4-carboxylic acid, L-threonine, 4-amino-3-hydroxy-2-methyl-$\eta$-valeric acid, $\beta$-hydroxy-histidine, $\beta$-amino-$\beta$-(4-amino-6-carboxy-5-methylpyrimidine-2-yl)-propionic acid, L-$\beta$-aminoalanine, L-gulose and 3-0-carbamoyl-D-mannose, which comprises hydrolyzing bleomycin in the presence of a mycelium mass or enzyme.

2 Claims, No Drawings

BLEOMYCINIC ACID AND PROCESS FOR PREPARING THEREOF

This application is a division of copending application Ser. No. 290,986, filed on Sept. 21, 1972, now U.S. Pat. No. 3,867,257. The latter application was a continuation-in-part of copending application Ser. No. 252,252, filed on May 11, 1972, now U.S. Pat. No. 3,843,448.

BACKGROUND OF THE INVENTION

1. Field of the Invention:

This invention relates to bleomycinic acid and to a process for preparing same.

2. Description of the Prior Art:

Bleomycin, antitumor antibiotics are water-soluble basic glycopeptides which are chelated with divalent copper, and are produced from *Streptomyces verticillus*. They were first discovered by Hamao Umezawa, et al., in 1966, and reported in *Journal Of Antibiotics* 19A, Page 200 (1966).

Sixteen varieties of bleomycins, including 3-dimethylsulfopropylamino-bleomycin (bleomycin $A_2$) and 4-guanidinobutylamino-bleomycin (bleomycin $B_2$), have been produced and isolated by conventional cultivation methods including bleomycin $A_1$, $A_2$, $A_5$ and $B_2$. These latter varieties have been used in complex form for the treatment of cancroid, malignant lymphoma and cerebral tumors, and exhibit antitumor effects and broad cancer indications.

By hydrolysis techniques, the chemical analysis of the bleomycins have been noted as follows:

microbial activity, antitumor activity and other physiological activity of these closely related bleomycins, however, are quite different, depending upon the particular amine side chain R in the formula.

When the bleomycin-producing strain of actinomycetes is inoculated and cultivated in a nutritious medium, bleomycins can be produced as complexes of bleomycin $A_1$, $A_2$, $A_5$, $B_2$, etc. If an amine, which corresponds to the side chain amine of the intended bleomycin is added, as a precursor, a bleomycin having the corresponding amine can be produced. Of course, the particular type of amine used is limited by ordinary considerations of biosynthesis, so that the range of possible amine derivatives attainable has been particularly limited. The type of biological activity will substantially vary, depending upon the particular variety of bleomycin and hence methods of developing different varieties are continually being sought.

To attain a wider latitude in the preparation of new amine derivatives, it was first contemplated to sever the side chain of the bleomycin without altering the basic nucleus structure, by enzyme reaction. It was found, however, that bleomycin cannot be used as a substrate for commercial or available hydrolysis enzymes such as peptidase, protease, pepsin, α-chymotrypsin, pronase, phytin, and amino acid acylase, and no severing of the side chain occurred.

Other microorganisms were studied as a means for producing an enzyme which would sever the side chain of bleomycin, and a wide variety of bacteria, actinomycetes and molds were considered.

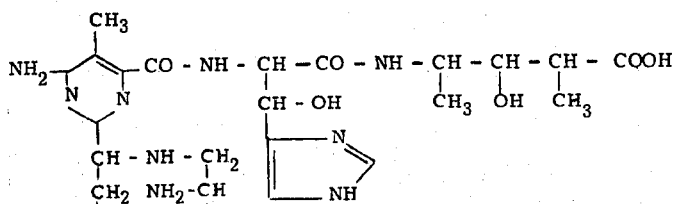

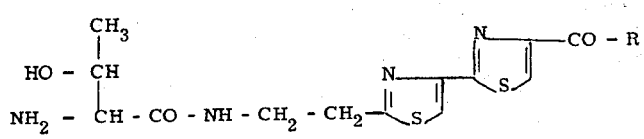

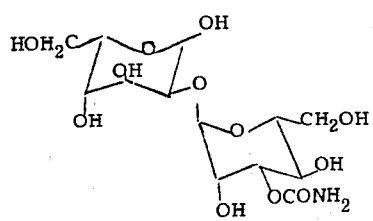

The various types of bleomycins differ by differing terminal amino group "R". In the present invention, R is an —OH group. Many of the bleomycins have the same basic nucleus but different side chain amines. The It has now been discovered that specific mycelium molds having high decomposition activities can be used to provide an enzyme reaction which will provide novel bleomycinic acid compounds.

SUMMARY OF THE INVENTION

Accordingly, it is one object of this invention to provide novel varieties of bleomycinic acid.

It is another object of this invention to provide a process for preparing said novel varieties of bleomycinic acid.

It is a still further object of this invention to provide bleomycins by reacting bleomycinic acid with an amine.

These and other objects of this invention, as will hereinafter become more readily apparent, have been attained by hydrolysis of bleomycin in the presence of a mycelium of the Fusarium genus, or Helminthosporium, or enzyme system thereof, or a medium containing same, to provide novel bleomycinic acid.

DETAILED DESCRIPTION OF THE PREFERRED EMBODIMENTS

The strain used for this invention is a type of Fungi imperfecti which belongs to the Fusarium genus, such as *Fusarium roseum* Link emend Snyder et Hansen IFO 7189 ATCC 20352 (W. C. Synder, H. N. Hansen., American J. Bot. Vol. 32 Page 657,666 (1945)), all of which are available *Fusarium roseum* Link emend Snyder et Hansen IFO 8502 (ibid), ATCC 20355

*Fusarium anguioides* Sherbakoff IFO 4467 ATCC 20351 (H. W. Wollenweber, Die Fusarien, Page 61, Berlin, 1965) etc.; and Helminthosporium genus such as *Helmintosporium zonatum* Ikata et Yoshida IFO 6678 ATCC 20353 (Ikata Yoshida BYOCHUGAIZASSHI, (Japan) Vol. 30, No. 7, Page 209(1943))

*Helmintosporium zonatum* Ikata et Yoshida IFO 7521 ATCC 20354 (ibid).

These strains may be aerobically cultivated in a medium suitable for molds. The productivity of the enzyme will not be seriously affected by the particular carbon source or nitrogen source. For example, the yield of mycelium and the yield of enzyme will be increased when the strain is grown in a medium containing a high content of glucose as a carbon source and peptone or corn steep liquor as the nitrogen source.

It is possible to use the mycelium or the mycelium cultured broth per se, for hydrolysis of the bleomycin to obtain the desired bleomycinic acid. However, when a purified enzyme having high activity is used, the formation of impurities can be reduced, and the concentrate of the substrate can be increased so that the reaction period can be shortened.

The strain growth period is preferably from 48 to 72 hours. The optimum temperature is 25° – 30°C., and the optimum pH is 6.0 – 7.0.

In the hydrolysis of bleomycin, the above-mentioned mycelium, or enzyme, is suspended or dissolved in a buffer solution of potassium phosphate, and is admixed with a solution of bleomycin in a buffer solution containing potassium phosphate. The mixture is then reacted for 2 – 10 hours. The optimum condition for hydrolysis of bleomycin is at a temperature of 25° – 45°C. in a 0.05 M potassium phosphate buffer solution, concentration of substrate 0.1 – 0.5%, at a pH of 7.0 – 8.0.

The endpoint of the hydrolysis reaction can be determined by a reaction in antimicrobial activity of the bleomycin substrate as measured by conventional cup tests using Mycobacterium 607, or by a change in the $R_f$ value during thin layer chromatography.

Following the reaction, impurities are removed and the product is adsorbed onto a weak acidic ion-exchange resin, such as Amberlite IRC-50[$H^+$] (trade name of Rohm & Haas Co.), and then is washed with water and is eluted with dilute hydrochloric acid. It is then neutralized and demineralized. Demineralization can be carried out by adsorption of the product on activated carbon (chromatography) grade, washing with water and then eluting with a 50% acetone-0.02 N-hydrochloric acid solution. Alternatively, demineralization can be carried out by adsorption of the product on an ion-exchange resin such as Amberlite CG-50[$H^+$]; (trade name of Rohm & Haas Co.), and then washing with 0.2% acetic acid or water followed by elution with a mixture of 50% methanol — 0.02 N—HCl.

The demineralized effluent is concentrated and dried and is dissolved in 0.05 M-ammonium chloride and the product is contacted with CM-Sephadex C-25 (trademark) or a dry insoluble powder composed of microscopic beads which are synthetic organic compounds derived from a polysaccharide dextran, (manufactured and sold by Pharmacia Fine Chemicals, Inc.) buffered with 0.05 M-ammonium chloride, and extracted with 0.05 M-ammonium chloride. The product, bleomycinic acid, is collected and is demineralized using said demineralization method. The solution is concentrated and dried at 40°C. under reduced pressure to obtain a high yield of pure hydrochloride of bleomycinic acid in powder form.

In order to confirm the bleomycinic acid, the following tests were carried out:

The resulting bleomycinic acid was hydrolyzed at 105°C. for 24 hours in 6N—HCL and the hydrolyzed product was developed using a high voltage paper electrophoresis method and paper chromatography.

By the ninhydrin reaction test of said paper chromatogram of acid hydrolyzed product of bleomycinic acid, the ninhydrin positive components were found in the same pattern as that of the original bleomycin $B_2$, except for a spot corresponding to the side chain of amine. The hydrolyzed products consist of 2'-(2-aminoethyl)-2,4'-bithiazole-4-carboxylic acid, L-threonine, 4-amino-3-hydroxy-2-methyl-n-valeric acid, β-hydroxy-histidine, and β-amino-β (4-amino-6-carboxy-5-methylpyrimidine-2-yl)-propionic acid, L-β-aminoalanine, L-gulose, and 3-o-carbamoyl-D-mannose. When the resulting bleomycinic acid was subjected to methanolysis in the presence of a strong acidic ion-exchange resin (Amberlyst 15, trade name) as a catalyst, and then trimethylsilylated, it was found that the product contained 1 mole of each of the components of L-gulose and 3-o-carbamoyl-D-mannose, when measured by gas chromatography.

When the resulting bleomycinic acid was esterified in methanol in the presence of hydrochloric acid as a catalyst, and then was reduced with $LiBH_4$ in anhydrous tetrahydrofuran and further hydrolyzed in the presence of an acid, it was found that an alcohol was formed by reducing the carboxyl group of 2'-(2-aminoethyl)-2,4'-bithiazol-4-carboxylic acid of the terminal amino acid of bleomycinic acid.

The aqueous solution of the resulting bleomycinic acid (95 mg./2.4 ml.) was admixed with 5 equivalents of 1-ethyl-3-(3-dimethylaminopropyl)carbodiimide and 10 equivalents of agmatine sulfate while cooling on ice and the mixture was adjusted to a pH of 7.0. The temperature was adjusted to 5°C. and the mixture was permitted to stand overnight. The reaction product was contacted with CM-Sephadex C-25, in a packed column and was eluted with 0.63 – 0.65 M-ammonium chloride solution, to yield 8 mg. of bleomycin having an antimicrobial activity of 3015 µ/mg. to Mycobacterium 607.

According to chromatographic behavior and the result of analysis of the acidic hydrolyzed product, the resulting bleomycin was confirmed to be the same as bleomycin $B_2$. The antimicrobial activity of bleomycin $B_2$ was 3094 µ/mg. It was thus confirmed that the resulting product was the intended bleomycinic acid.

The hydrochloride of bleomycinic acid is soluble in water and sparingly soluble in methanol, acetic acid, dimethylsulfoxide, and insoluble in ethanol, ethyl acetate, acetone and ether.

The physico-chemical properties of the compound are as follows:

Melting point 228° – 230°C. (decomposition)

$[\alpha]_{436}^{26} = 81.5°$ (C = 0.1, $H_2O$)

Elementary Analysis: C: 40.80%, H : 5.29%, N : 16.45%, O : 24.78%, S : 4.53%, Cl : 3.37%, Cu : 4.78%.

oped with a system of 15 : 10 : 3 : 12 of n-propanol : pyridine : acetic acid : water.

The bleomycinic acid showed an $R_f$ value of 0.86 in paper chromatography using a Toyo filter paper No. 51 when developed with 10% ammonium chloride, and also showed an $R_m$ value of 0.65 in paper electrophoresis at 3000 V for 40 minutes when developed with a system of 25 : 75 : 900 of formic acid : acetic acid : water. ($R_m$ of alanine is 1.0). By a cup test using Mycobacterium 607, the anti-microbial activity of the product was relatively low, being 159 µ/mg., as compared with the standard of bleomycin $A_2$, 1000 µ/mg.

Various novel bleomycin compounds can be prepared using the resulting bleomycinic acid. For example, the bleomycinic acid can be reacted with a variety of amines to yield various bleomycin compounds having the corresponding amines in the side chain. These bleomycins may exhibit excellent antimicrobial activities to Mycobacterium 607, some being different from the known bleomycins.

Bleomycinic acid may be reacted with benzylamine to yield benzylamino-bleomycin.

The structure of bleomycinic acid is:

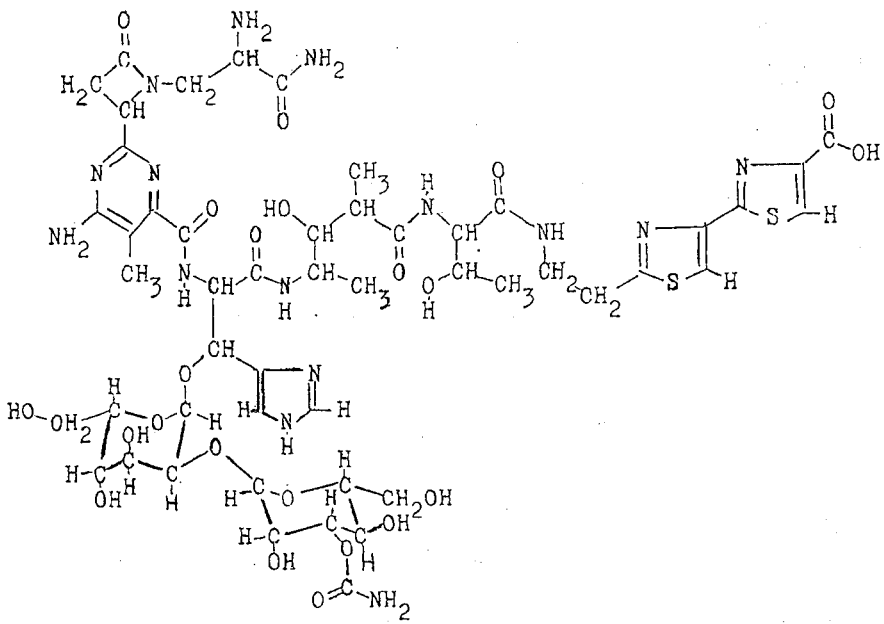

The ultraviolet absorption spectrum of the hydrochloride of bleomycinic acid is slightly different from that of the starting material of bleomycin, wherein the maximum absorption, respectively, is at 246 mµ and 292 mµ and $E_{1cm}^{1\%}$ respectively, is 140.0 and 137.5.

The infrared absorption spectrum of the product measured as potassium bromide tablet. Bands are found at 3350, 1720, 1670, 1640, 1580, 1460, 1365, 1050, 770 (cm$^{-1}$).

The bleomycinic acid showed positive in Pauly and Ehrlich reaction, but provided negative results in ninhydrin reaction. Sakaguchi reaction, Dragendorf reaction, Tollens reaction, ferric chloride reaction, Fehling and Molisch reactions.

The bleomycinic acid showed an $R_f$ value of 0.78 in thin layer chromatography using silica gel G when developed with a system of 10 : 9 : 1 of methanol : 10 % ammonium acetate: 10 % ammonia. It also showed an $R_f$ value of 0.46 in thin layer chromatography devel- The experimental results of biological activity of the benzylaminobleomycin (the terminal amino group R is benzylamino group) will be illustrated as compared with the above-mentioned bleomycin $B_2$.

Preparation of benzylamino-bleomycin 48.64 mg. (0.038 m mole) of bleomycinic acid and 45.31 mg. (0.38 m mole) of benzylamine were dissolved in 1 l. of water and the solution was cooled to 0° – 5°C. It was then admixed with 28.40 mg. (0.19 m mole) of a water soluble carbodiimide and the solution was adjusted to a pH of 4.5 with 6N—HCl. It was then reacted for 30 minutes, with stirring. After the reaction, the reaction mixture was maintained at 0° – 5°C. for 24 hours. The resulting benzylamino-bleomycin was separated and purified, in accordance with the preparation of bleomycin $B_2$ from bleomycinic acid, to yield 15.2 mg. of benzylamino-bleomycin having a microbial activity to Mycobacterium 607 of 3250 $\mu$/mg. By chromatographic analysis and by analysis of the acid-hydrolyzed products, it was confirmed that the product was benzlyamino-bleomycin.

(Experiment)

The above benzylamino-bleomycin or bleomycin $B_2$ was administered to ICR-JCL male mice by intravenous injection at a rate of 10 mg./kg. over a period of 10 days. The mice were bred for 5 weeks after the final administration and were then dissected. The right and left lungs were observed by microscopic examination. The degree of fibrosis in the lung is shown in Table 1.

| Concentrations | Inhibitory effect | | | |
|---|---|---|---|---|
| | 5 | 2.5 | 1.25 | 0.625(mcg/ml) |
| Bleomycin $B_2$ | 74.9 | 56.0 | 34.0 | 8.6 |
| Benzylamino-bleomycin | 83.5 | 55.4 | 28.2 | 11.1 |

These results show the effectiveness of the benzylamino-bleomycin against tumors.

Having generally described the invention, a more complete understanding can be attained by reference to certain specific Examples which are provided herein for purposes of illustration only and are not intended to be limiting in any manner unless otherwise so specified.

TABLE 1

| | Lung | Mouse | | | | | | | |
|---|---|---|---|---|---|---|---|---|---|
| | | 1 | 2 | 3 | 4 | 5 | 6 | 7 | 8 |
| Bleomycin $B_2$ | L | + | | + | | ++ | | − | |
| | R | − | | + | | ± | | ± | − |
| Benzylamino Bleomycin | L | − | | − | | + | | − | |
| | R | − | | − | | − | | − | |

| | Lung | Mouse | | | | | | | |
|---|---|---|---|---|---|---|---|---|---|
| | | 9 | 10 | 11 | 12 | 13 | 14 | 15 | 16 |
| Bleomycin $B_2$ | L | ± | | − | | − | | − | |
| | R | ± | | − | | + | | − | |
| Benzylamino Bleomycin | L | − | | − | | − | | − | |
| | R | ± | | ± | | − | | − | |

| | Lung | Mouse | | | | Total | | | |
|---|---|---|---|---|---|---|---|---|---|
| | | 17 | 18 | 19 | 20 | − | ± | ± | ++ |
| Bleomycin $B_2$ | L | + | − | | | 5 | 1 | 3 | 1 |
| | R | − | + | | | 4 | 3 | 3 | 0 |
| Benzylamino Bleomycin | L | | ± | | | 8 | 1 | 1 | 0 |
| | R | | ± | | | 7 | 3 | 0 | 0 |

The toxicity of the benzylamino-bleomycin was lower than that of bleomycin $B_2$.

(Experiment 2)

The benzylamino-bleomycin and bleomycin $B_2$ respectively, showed the following inhibitory effect against cell culture of HeLa ($S_3$bb cell line)

| Concentrations | Inhibitory effect | | |
|---|---|---|---|
| | 6 | 3 | 1.5 (mcg/ml.) |
| Bleomycin $B_2$ | 92 | 64 | 33 |
| Benzylamino-bleomycin | 92 | 73 | 38 | wherein the inhibitory effect =

$$\frac{t_3 - C_o}{C_3 - C_o} \times 100;$$

$C_o$: relative number of cell on the first day $t_3$ : relative number of cell on the third day after the addition of a bleomycin (3 mcg/ml in final)

$C_3$ : relative number of cell in negative control on the third day

The benzylamino-bleomycin and bleomycin $B_2$ were respectively tested on the cell culture of Yoshida (the method described by M. Hori, et al., *Journal Of Antibiotics Ser. A.* Vol. 16, No. 1, Page 1). The results were as follows:

EXAMPLE 1

A medium consisting of 5% glucose, 0.4% peptone, 0.05% corn steep liquor, 0.03% magnesium sulfate, 0.1% potassium hydrophosphate, 0.01% sodium chloride, 0.01% calcium chloride and 0.001% ferric chloride, was adjusted at pH 6.0 and 10 ml. of the medium was charged into a 100 ml. Sakaguchi flask and was sterilized at 120°C. under 1 atm. for 15 minutes.

The medium was inoculated with a platinum loop of *Fusarium roseum* Link emend Snyder et Hansen (IFO 7189), deposited in the Institute for Fermentation (Osaka, Japan), ATCC 20352, cultured in slant, and was shake-cultured at 27°C. for 72 hours.

100 ml. of the medium having the same formula was charged to each of the 500 ml. Sakaguchi flask and was sterilized under the same conditions. 0.2 ml. of a spore medium resulted was added to each medium and was shake-cultured.

The cultured broths were collected 3 days after initiation of the cultivation, and were filtered to yield 15 g./l. of a mycelium mass. 100 g. of the mycelium mass was suspended in 200 ml. of 0.02 M-potassium phosphate buffer solution of pH 7.0 and then the mycelium mass was broken by a Frenchpress at a cool temperature and was separated in conventional freezing centrifugal separation at 19000 G.

The resulting supernatant liquid was admixed with solid ammonium sulfate to yield a 75% saturated solution, and 2.3 g. of the precipitated enzyme was dissolved in a potassium phosphate buffer solution having a pH of 7 and was purified by dialysis with the same buffer solution to yield an enzyme solution.

5 g. of bleomycin $B_2$ was dissolved in 0.05 M-potassium phosphate buffer solution and was admixed with said enzyme solution to make a total amount of 500 ml. of solution. The mixture was reacted at 35°C. for 2 hours and was charged to a column 2 cm. in diameter and 50 cm. in length, packed with Amberlite IRC-50[H$^+$] to adsorb the product. After washing with water, the product was eluted with 0.2 N—HCl and the effluent was neutralized and then was charged to a column 2 cm. in diameter and 20 cm. in length, packed with activated carbon for chromatography adsorption of the product.

After washing with water, the product was eluted with a mixture of 50% acetone-0.02 N—HCl, and the effluent was concentrated and dried at 40°C. under reduced pressure. The residue was dissolved in a small amount of 0.05 M-ammonium chloride, and was adsorbed with CM-Sephadex C-25 which was buffered with 0.05 M-ammonium chloride. 0.05 M-ammonium chloride was passed through the layer to separate bleomycinic acid. The bleomycinic acid solution was collected and demineralized and was concentrated and dried at 40°C. under reduced pressure, to yield 900 mg. of hydrochloride of bleomycinic acid having 228° – 230°C. melting point (decomposition) in powdered form.

EXAMPLE 2

*Helmintosporium zonatum* Ikata et Yoshida (IFO 7521) deposited in the Institute of Fermentation (Osaka, Japan) ATCC 20354, was cultured in accordance with the process of Example 1, to yield a mycelium mass.

200 g. of the mycelium mass and 10 g. of bleomycin $B_2$ were admixed with 250 ml. of 1 M-potassium phosphate buffer solution having a pH of 7.5. 10 ml. of toluene and water were added to the mixture to make a total solution of 500 l. The mixture was stirred and then permitted to stand at 37°C. for 12 hours.

The reaction solution was filtered under reduced pressure and was washed with water and the filtrate was charged in a column, 2.6 cm. in diameter and 70 cm. in length, packed with Amberlite IRC-50[H$^+$] (trade name) to adsorb the product.

After washing with water, the product was eluted with 0.2N—HCl and the effluent was adjusted to a pH of 7, and was charged to a column 2.6 cm. in diameter and 70 cm. in length, packed with Amberlite CG-50[H$^+$] to adsorb the product. After washing with 0.2% acetic acid, the product was eluted with a mixture of 50% methanol-0.02 N—HCl. The effluent was concentrated and dried at 40°C. under reduced pressure. The residue was dissolved in 0.05 M-ammonium chloride and was adsorbed on CM-Sephadex C-25.

0.05 M-ammonium chloride was passed through the layer to collect the bleomycinic acid solution. The solution was concentrated and dried under reduced pressure to yield 3.5 g. hydrochloride of bleomycinic acid having a melting point of 228°–230°C. (decomposition) in powdered form.

EXAMPLE 3

*Fusarium anguioides* Sherbakoff (IFO 4467) deposited in the Institute for Fermentation (Osaka, Japan), ATCC 20351, was cultured in accordance with the process of Example 1, to yield 10 g. of a mycelium mass per 1 l. of cultured broth.

100 g. of the mycelium mass and 5 g. of complex of bleomycin were dissolved in 2.5 l. of 0.05 M-potassium phosphate buffer solution and was admixed with 5 ml. of toluene and was well stirred. The mixture was permitted to stand at 40°C. for 12 hours. The insoluble material was removed from the reaction solution to yield a clear filtrate.

In accordance with the process of Example 2, the filtrate was purified to yield 1.1 g. of hydrochloride of bleomycinic acid having a melting point of 228° – 230°C. (decomposition) in powdered form.

Having now fully described the invention, it will be apparent to one of ordinary skill in the art that many changes and modifications can be made thereto without departing from the spirit or scope of the present invention as set forth herein. Accordingly,

What is claimed and desired to be secured by Letters Patent is:

1. A compound having the structure of:

2. Bleomycinic acid having a melting point of 228°–230°C. (decomposition) and an analysis of C : 40.80%, H : 5.29%, N : 16.45%, O : 24.78%, S : 4.53%, C : 3.37%, and Cu : 4.78% which is soluble in water, difficultly soluble in methanol, acetic acid and dimethylsulfoxide, and which is insoluble in ethanol, ethylacetate, acetone and ether, and which tests positive in Pauly and Ehrlich reactions but tests negative in ninhydrin, Sakaguchi, Dragendorf, Tollens, ferric chloride, Fehling and Molisch reactions, and which has maximum adsorption in the ultraviolet absorption spectrum at 246 m$\mu$ and 292 m$\mu$ and which has infrared absorption spectrum bands at 3350, 1720, 1670, 1640, 1580, 1460, 1365, 1050, 770 (cm$^{-1}$) and can be hydrolyzed to yield 2'-(2-aminoethyl)-2,4'-bithiazole-4-carboxylic acid, L-threonine, 4-amino-3-hydroxy-2-methyl-$\eta$-valeric acid, $\beta$-hydroxy-histidine, $\beta$-amino-$\beta$-(4-amino-6-carboxy-5-methylpyrimidine-2-yl)-propionic acid, L-$\beta$-amino-alanine, L-gulose and 3-o-carbamoyl-D-mannose.

\* \* \* \* \*